United States Patent [19]

Mericle

[11] 4,343,306
[45] Aug. 10, 1982

[54] CLEANING DEVICE FOR SYRINGE TYPE NEEDLES

[76] Inventor: Gerald E. Mericle, 130 Second St., Hamden, Conn. 06514

[21] Appl. No.: 236,834

[22] Filed: Feb. 23, 1981

[51] Int. Cl.³ .............................................. A61M 5/00
[52] U.S. Cl. ................................ 128/218 N; 128/221
[58] Field of Search ........... 128/218 R, 218 N, 218 S, 128/215, 216, 220, 221, 234

[56] References Cited

U.S. PATENT DOCUMENTS 2,845,068  7/1958  Gabriel ...................... 128/218 N X
2,879,766  3/1959  Wilburn ........................ 128/218 S
3,406,686  10/1968  Keller .......................... 128/218 S X
4,142,525  3/1979  Binard et al. ................... 128/218 R Primary Examiner—John D. Yasko
Attorney, Agent, or Firm—DeLio and Libert

[57] ABSTRACT

A cleaning device for re-usable surgical needles of the type wherein a needle having a hub is sheathed in a cannula also having a hub, the hubs being designed to interfit in use and the cleaning device comprising adapters which direct cleaning liquid forcibly from a syringe against and/or past all areas of the needle and cannula, and their hubs, which might require cleaning.

5 Claims, 10 Drawing Figures

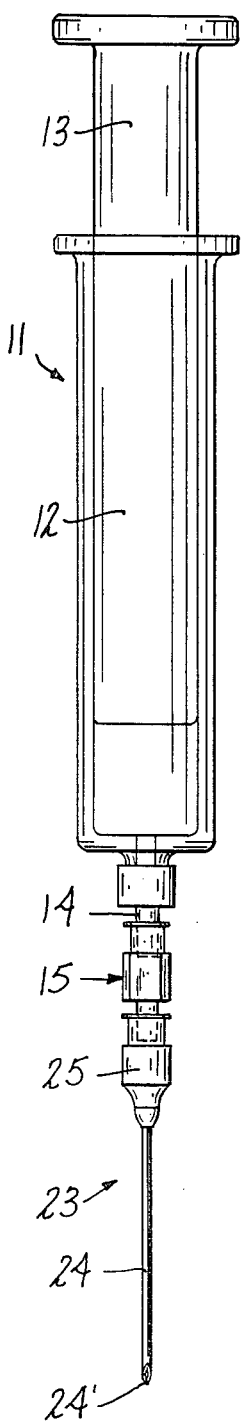
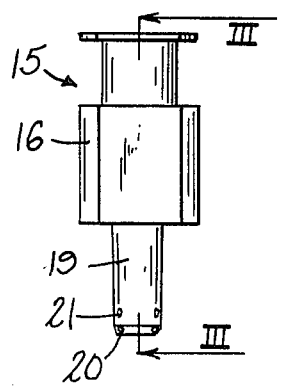
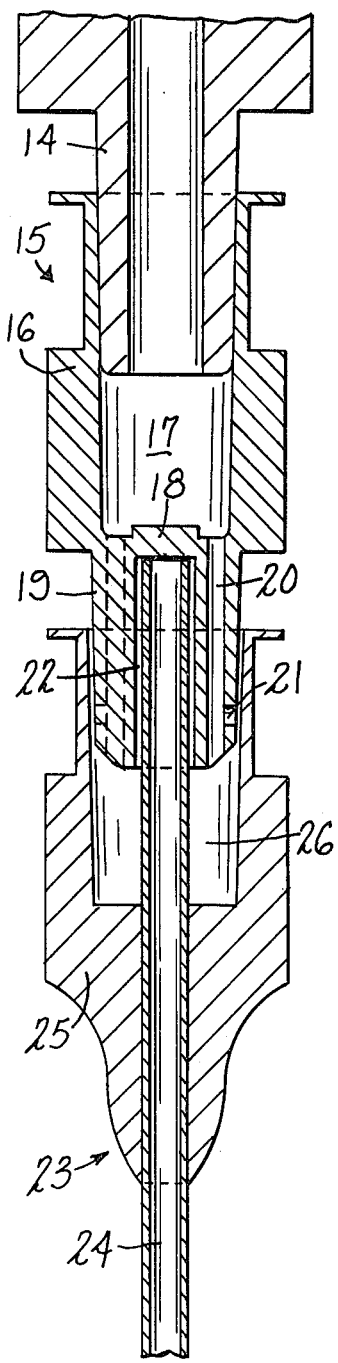
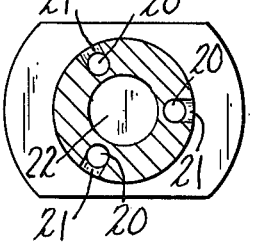

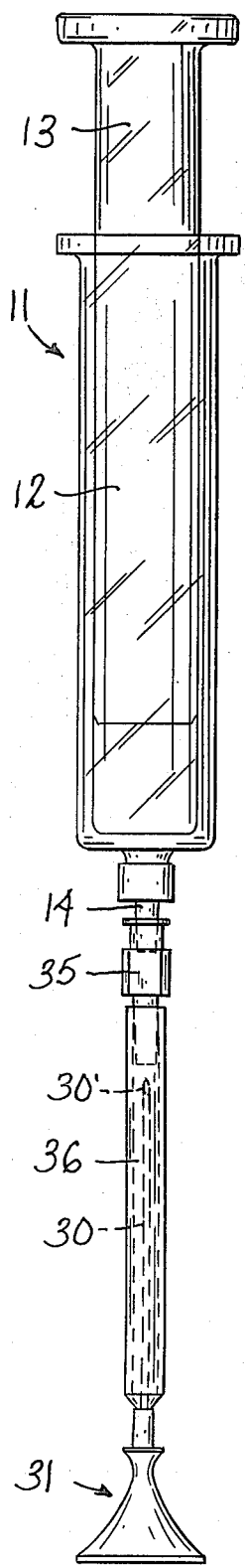
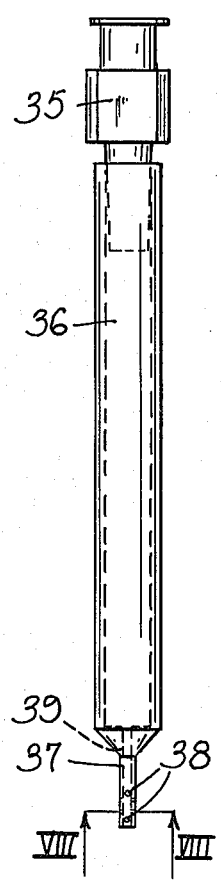
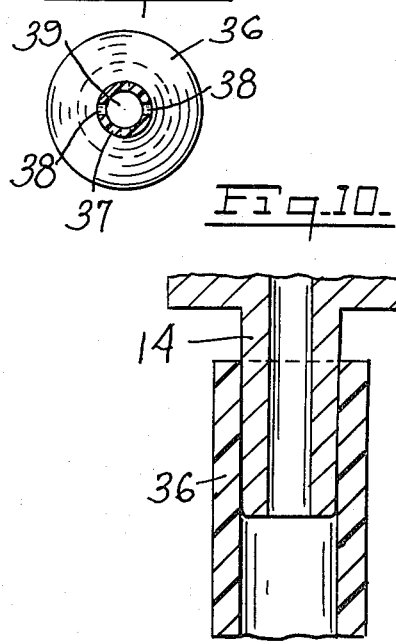
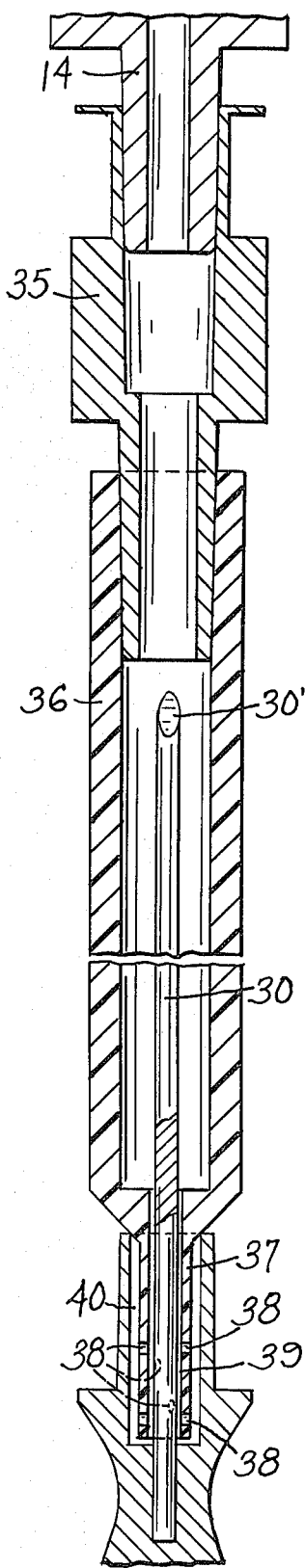

CLEANING DEVICE FOR SYRINGE TYPE NEEDLES

This invention relates to a cleaning device for surgical needles, particularly such needles as are intended to be re-usable as distinguished from the disposable needles commonly used for intravenous injections and similar purposes.

A good example of a re-usable needle assembly to which the present cleaning device is applicable is the so-called "Bierman needle" wherein a slightly curved, bevel-pointed needle element is sheathed in a similarly curved bevel-pointed cannula with the beveled points in register to present an effective entry surface adjacent the sharpened distal tip. Both elements are normally of surgical grade stainless steel and the cannula has an integral hub while the needle is provided with a combined hub and a suitably shaped handle. Such a needle assembly is normally used for withdrawing specimens (bone marrow, body fluids, tissue, etc.) from a body rather than injection of medicaments or the like, and specimen fragments tend to become lodged in recesses of the hubs as well as on the interior surface of the cannula bore and exterior surface of the needle. The cleaning expedients heretofore resorted to, as by the use of swabs, are not satisfactory or fully effective so that the present cleaning device fills a very real need.

It is accordingly an object of the invention to provide a set of cleaning elements adapted for use in effecting the thorough flushing and rinsing of both parts of a Bierman needle or the like.

It is another object of the invention to provide needle cleaning elements which are adapted to guide a cleaning liquid, under pressure, effectively into recessed areas of a needle and/or cannula hub.

It is a further object of the invention to provide needle cleaning elements which can, themselves, be cleaned in a conventional manner and wet or dry sterilized.

It is yet another object of the invention to provide certain improvements in the form, construction, arrangement, and materials of the parts whereby the above-named and other objects may effectively be attained.

The invention accordingly comprises an article of manufacture possessing the features, properties, and the relation of elements which will be exemplified in the article hereinafter described, and the scope of the invention will be indicated in the claims.

The cleaning device comprises elements which, when assembled with a suitably filled syringe, can subject each part of the needle assembly to a forceful flushing and rinsing action with efficient use of the cleaning liquid and only controlled spillage. For use on the soiled cannula, an adapter device carried by the syringe has a nozzle portion with longitudinal and lateral passages through which the cleaning liquid can be forced in a manner to flush out the chamber in the proximal end of the cannula hub as well as the adjacent end and interior of the cannula itself. For cleaning the needle, the syringe is equipped with a two-part adapter comprising a metal element fitting on the syringe nozzle and an elongated tubular plastic element fitting on the metal element and terminating distally in an extension having longitudinal and lateral passages so that, when the needle has been inserted through the extension into the tubular element, the cleaning liquid from the syringe can be forced past the entire length of the needle and circulated into the cavity formed in the distal face of the needle hub.

A practical embodiment of the invention is shown in the accompanying drawings, wherein:

FIG. 1 represents an elevational view of a standard syringe with a Bierman needle cannula to be cleaned mounted thereon by the interposition of a special adapter;

FIG. 2 represents an elevation of the special adapter alone;

FIG. 3 represents a longitudinal section on a larger scale, taken on the line III—III of FIG. 2;

FIG. 4 represents a transverse section taken on the line IV—IV of FIG. 3;

FIG. 5 represents a detail axial section on the same scale showing the parts assembled for the cleaning operation, parts being broken away;

FIG. 6 represents an elevational view of a standard syringe with a Bierman needle element to be cleaned engaged in the plastic portion of a special two-part adapter;

FIG. 7 represents an elevational view of the two-part adapter alone;

FIG. 8 represents a cross-sectional view, on a larger scale, on the line VIII—VIII of FIG. 7;

FIG. 9 represents a detail axial section, on the same scale, showing the parts assembled for the cleaning of a needle element, parts being broken away, and FIG. 10 represents a detail sectional view showing the attachment of the plastic cleaning adapter directly to the syringe, without use of the metal adapter element.

Referring to the drawings, and particularly to FIGS. 1 to 5, a syringe 11, of conventional form, is shown as having a barrel 12, plunger 13, and nozzle 14.

The cannula cleaning adapter 15 comprises a cylindrical body portion 16, having an internal chamber 17 sized to fit snugly on the syringe nozzle 14 and closed at the bottom by a flat wall 18. Below the wall 18 is an extension 19, the cylindrical wall of which is traversed longitudinally by a plurality of bores 20 (three being shown) each bore being vented radially outward near its distal end as shown at 21. The extension wall defines a distally open recess 22.

In the Bierman needle assembly the cannular element 23 comprises a tube 24 mounted in a hub 25 provided with a proximally facing cylindrical recess 26 from which the proximal end of the tube may protrude axially, as indicated in FIG. 5.

For cleansing this element 23 after use, the adapter 15 is mounted on the nozzle 14 of a syringe loaded with cleaning liquid; the extension 19 is introduced loosely into the recess 26 (FIG. 5) and the liquid is expelled forcibly from the syringe barrel. As will be apparent from FIG. 5, the liquid from the syringe nozzle traverses a course through the chamber 17, bores 20, vents 21, recess 26, and recess 22, some of the liquid entering the proximal end of the tube adjacent the wall 18 and some escaping through the clearance which is provided between the outer surface of the extension 19 and the wall of the hub recess 26. The scouring action of the liquid can be proportioned between the tube bore and hub recess by varying the spacing of the wall 18 from the tube end.

Referring to FIGS. 6 to 10, the needle element in a Bierman needle assembly comprises a plain shaft 30 and a combined hub and handle 31, the hub portion having a deep cylindrical recess 32 and the needle shaft being mounted securely, at its proximal end, in the bottom of the recess. The outer surface of the hub is cylindrical and sized to fit snugly in the recess 26 of the cannula hub when the needle elements are assembled for use, with the proximal end of the cannula extending into the needle hub recess 32. At their distal ends both elements are beveled as shown at 24', 30' and their respective hubs are provided with conventional lug and notch means, not shown, to ensure accurate registry of the beveled points.

For cleaning the needle element a simple metal adapter 35 (like adapter 15 but without bores 20 and vents 21) is mounted on the syringe nozzle 14 and an elongated tubular plastic element 36 is mounted on the adapter 35. The tubular element terminates in an extension 37 of reduced internal and external diameters. The extension is shown as being provided with a plurality of radial vents 38 and its size permits it to be assembled on the needle with the needle shaft 30 passing freely through the bore 39 while clearance 40 is also provided between the outer wall of the extension and the side wall of the recess 32, as clearly shown in FIG. 9.

The provision of the metal adapter 35, between the syringe and the plastic element 36 is considered to be desirable for improved stability of the latter, but the plastic element can, if desired, be mounted directly on the syringe nozzle, as shown in FIG. 10.

In use, for cleansing the needle element and its hub, the parts are assembled as shown in FIGS. 6 and 9, the syringe is actuated to expel cleaning liquid through the adapter 35 (if used) into the bore of the tubular plastic element 36 and extension 37 where it thoroughly washes and rinses the exterior of the needle 30. Within the recess 32 the liquid fills the clearance 40 and exits as spillage through a gap (not shown) which can be provided at the rim of the recess by relaxing the manual pressure of the cleaning assembly against the needle hub.

Description of the vents 21 and 38 as "radial" is intended to indicate only that they extend outward from an inner bore or passage to the outer surface (substantially cylindrical or slightly tapered) of the adapter extension, without limitation as to the precise angle between the vent axes and the axis of the adapter.

It will thus be seen that the objects set forth above, among those made apparent from the preceding description, are efficiently attained and, since certain changes may be made in the above article without departing from the spirit and scope of the invention, it is intended that all matter contained in the above description and shown in the accompanying drawings shall be interpreted as illustrative and not in a limiting sense.

What I claim is:

1. A cleaning device for surgical needles in combination with a syringe having a nozzle, said device comprising an adapter adapted for operative engagement with the syringe nozzle, the adapter including an axially extending portion having a substantially cylindrical outer wall, an axially extending passage in said portion and at least one radially disposed vent extending from said passage through said wall, the adapter being provided further with a proximally open chamber adapted to receive a syringe nozzle, a distally open chamber and a transverse wall between said chambers.

2. A cleaning device according to claim 1 wherein the axially extending portion is traversed by a plurality of axially extending passages adjacent to the distally open chamber and wherein a radially disposed vent intersects each said passage.

3. A cleaning device according to claim 2 wherein the distally open chamber is sized to receive loosely a projecting proximal end of a cannula and the cylindrical outer wall of the axially extending portion is sized to fit loosely within the hub of a cannula.

4. A cleaning device for a surgical needle having a hub with a recess in combination with a syringe having a nozzle, said device comprising an elongated adapter adapted for operative engagement with the syringe nozzle, the adapter including an axially extending portion having a substantially cylindrical outer wall, an axially extending passage in said portion and a plurality of radially disposed vents extending from said passage through said wall, the adapter being provided with an axially extending passage sized to receive freely the shaft of a needle, and the axially extending portion being sized to be received freely within the recess in the needle hub.

5. A cleaning device assembly for use with a syringe having a nozzle to clean a needle and cannula assembly wherein the needle is mounted in a distally chambered hub and the cannula is mounted in a proximally chambered hub, said cleaning device assembly comprising a first adapter adapted for operative engagement with the syringe nozzle, said adapter including an axially extending portion having a substantially cylindrical outer wall, an axially extending passage in said portion and a plurality of radially disposed vents traversing said wall, said cleaning device assembly further comprising a second adapter provided with a proximally open chamber adapted for operative engagement with the syringe nozzle, the adapter being further provided with an axially extending portion having a distally open chamber and a transverse wall between said chambers, the axially extending portion being traversed by a plurality of axially extending passages and by a radially disposed vent intersecting each said passage.

* * * * *